(12) United States Patent
Sutherland et al.

(10) Patent No.: US 11,276,001 B1
(45) Date of Patent: Mar. 15, 2022

(54) MACHINE LEARNING FOR INTERCONNECTED SURGICAL THEATER ARCHITECTURE

(71) Applicant: OrbSurgical Ltd., Calgary (CA)

(72) Inventors: Garnette R. Sutherland, Calgary (CA); Amir Baghdadi, Calgary (CA); Rahul Singh, Calgary (CA); Sanju Lama, Calgary (CA)

(73) Assignee: OrbSurgical Ltd., Calgary (CA)

( * ) Notice: Subject to any disclaimer, the term of this patent is extended or adjusted under 35 U.S.C. 154(b) by 0 days.

(21) Appl. No.: 17/344,813

(22) Filed: Jun. 10, 2021

(51) Int. Cl.
| | |
|---|---|
| *G06N 20/20* | (2019.01) |
| *G06F 21/62* | (2013.01) |
| *G06N 3/08* | (2006.01) |
| *G06N 3/04* | (2006.01) |
| *H04L 9/00* | (2022.01) |
| *A61B 34/10* | (2016.01) |
| *G06K 9/62* | (2022.01) |

(52) U.S. Cl.
CPC ............... *G06N 3/08* (2013.01); *A61B 34/10* (2016.02); *G06K 9/6262* (2013.01); *G06N 3/04* (2013.01); *H04L 9/008* (2013.01); *A61B 2034/102* (2016.02)

(58) Field of Classification Search
CPC .. G06F 12/1408; G06F 21/6245; G06F 21/64; G06F 2212/1052; G06F 2221/034; G06F 21/6254; G06N 20/00; H04L 63/0421; H04L 63/0428; H04L 63/107; H04L 9/0894; H04L 9/32; H04W 12/02
See application file for complete search history.

(56) References Cited

U.S. PATENT DOCUMENTS

| | | | | |
|---|---|---|---|---|
| 11,102,064 | B2 * | 8/2021 | Grant | .................... H04L 67/303 |
| 2019/0370687 | A1 * | 12/2019 | Pezzillo | ................. G06N 20/00 |

FOREIGN PATENT DOCUMENTS

| | | | | |
|---|---|---|---|---|
| CN | 113052333 | * | 6/2021 | ............. G06N 20/20 |

* cited by examiner

*Primary Examiner* — Tom Y Lu
(74) *Attorney, Agent, or Firm* — Jones Day (57) ABSTRACT

Each of a plurality of edge computing devices are configured to receive data streams generated by at least one sensor forming part of a respective medical device (e.g., a sensor-equipped surgical tool, etc.) which, in turn, characterizes use of the respective medical device in relation to a particular patient. Each of the edge computing devices can execute at least one machine learning model which generates or from which model attributes are derived. The generated model attributes are anonymized using an anonymization technique such as k-anonymity. The anonymized generated model attributes are homomorphically encrypted and transmitted to a central server. Encrypted model attribute updates to at least one of the machine learning models are later received from the central server which results in the machine learning models executing on one or more of the edge computing devices to be updated based on the received encrypted model attribute updates.

20 Claims, 6 Drawing Sheets

MACHINE LEARNING FOR INTERCONNECTED SURGICAL THEATER ARCHITECTURE

TECHNICAL FIELD

The subject matter described herein relates to a federated learning architecture for characterizing the use of sensor-equipped surgical instruments/systems and or medical device in surgical theaters digitally connected across different sites to improve patient outcomes.

BACKGROUND

According to the World Health Organization (WHO), surgical procedures lead to complications in 25% of patients (around 7 million annually) among which 1 million die. Among surgical tasks responsible for error, tool-tissue force exertion is a common variable. Surgical simulation has shown that more than 50% of surgical errors are due to the inappropriate use of force contributing to an annual cost of over $17 billion in the USA alone.

SUMMARY

In a first aspect, each of a plurality of edge computing devices generates model attributes. These edge computing devices are each configured to receive one or more data streams generated by at least one sensor forming part of a respective medical device (e.g., a sensor-equipped surgical tool, etc.) which characterizes use of the respective medical device in relation to a particular patient. Each of the edge computing devices can execute at least one machine learning model. The generated model attributes are anonymized using an anonymization technique such as k-anonymity. The anonymized generated model attributes are homomorphically encrypted and transmitted to a central server. Based on such transmitting, encrypted model attribute updates to at least one of the machine learning models are received from the central server which results in the updating of one or more of the machine learning models executing on one or more of the edge computing devices based on the received encrypted model attribute updates.

In an interrelated aspect, anonymized and encrypted model attributes, are received by a cloud server from each of a plurality of edge computing devices, anonymized and encrypted model attributes. These edge computing devices are each configured to receive one or more data streams generated by at least one sensor forming part of a respective medical device. The at least one sensor can characterize use of the respective medical device in relation to a particular patient. Further, each of the edge computing devices executes at least one machine learning model. The received model attributes are decrypted which can cause the cloud server to update model attributes for one or more cloud-based machine learning models corresponding to one or more machine learning models being executed by the edge computing devices. These updated model attributes can be encrypted and transmitted to the edge computing devices executing at least one machine learning model having updated model attributes. The corresponding edge computing device later decrypts the updated model attributes and updates the corresponding machine learning models based on the transmitted updated model attributes.

The model attributes can take various forms including model hyperparameters. Model hyperparameters can include one or more of: neural network hidden layer size, number of convolution layers, batch normalization specifications, or activation layer type. As another example, the model attributes can include model information. Model information can include one or more of: model name, data input and output characteristics, data dimensionality, training data size, testing data size, number of training iterations, learning rate, or optimization method.

The updating can include retraining the one or more of the machine learning models executing on one or more of the edge computing devices using the received encrypted updates. The received updates can include encrypted model hyperparameters.

In a further interrelated aspect, a plurality of edge computing devices communicated with a cloud-based computing system. The plurality of edge computing devices are each configured to receive one or more data streams generated by at least one sensor forming part of a respective medical device. The at least one sensor characterizes use of the respective medical device in relation to a particular patient. Each of the edge computing devices executes at least one machine learning model. The cloud-based computing system trains and updated the respective at least one machine model based on data received from the plurality of edge computing devices which has been anonymized and encrypted using homomorphic encryption prior to it being transmitted over a network by the edge computing devices. In addition, the cloud-based system sends updates over the network to the machine learning models being executed on the edge computing devices.

A plurality of Internet of the Operating Theaters (IoT-OR) gateways can provide communication interfaces between the edge computing devices and the cloud-based computing system to allow for the exchange of model attributes used for updating the respective machine learning models.

The IoT-OR gateways can relay data from the edge computing devices to the cloud-based computing system while, in other variations, the IoT-OR gateways can process data from the edge computing devices prior to transmission to the cloud-based computing system.

Non-transitory computer program products (i.e., physically embodied computer program products) are also described that store instructions, which when executed by one or more data processors of one or more computing systems, cause at least one data processor to perform operations herein. Similarly, computer systems are also described that may include one or more data processors and memory coupled to the one or more data processors. The memory may temporarily or permanently store instructions that cause at least one processor to perform one or more of the operations described herein. In addition, methods can be implemented by one or more data processors either within a single computing system or distributed among two or more computing systems. Such computing systems can be connected and can exchange data and/or commands or other instructions or the like via one or more connections, including but not limited to a connection over a network (e.g., the Internet, a wireless wide area network, a local area network, a wide area network, a wired network, or the like), via a direct connection between one or more of the multiple computing systems, etc.

The current subject matter provides many technical advantages. For example, the current techniques utilizing horizontal federated learning (i.e., a model in which data samples are unique but the feature space is shared across datasets) supports decentralized collaborative machine learning, prevents bias, maintains privacy of sensitive patient data and most important, and facilitates improved performance for local machine learning models using common features but with different sample instances.

The details of one or more variations of the subject matter described herein are set forth in the accompanying drawings and the description below. Other features and advantages of the subject matter described herein will be apparent from the description and drawings, and from the claims.

DETAILED DESCRIPTION

The current subject matter is directed to a federated, machine learning architecture and related techniques and systems for monitoring or otherwise characterizing use of a surgical instrument during one or more surgical procedures. While the current subject matter is described, as an example, in connection with sensor-equipped forceps, it will be appreciated that the current subject matter can also be used with other network connected medical devices and surgical instruments utilized within an operating room environment.

The current subject matter can be used with advanced machine learning models and advanced surgical instruments including sensor-equipped forceps such as that described in U.S. patent application Ser. No. 17/318,975 filed on May 14, 2021 and entitled: "Machine Learning-Based Surgical Instrument Characterization" and U.S. Pat. Pub. No. 20150005768A1 entitled: "Bipolar Forceps with Force Measurement", the contents of both of which are hereby incorporated by reference. The surgical instruments used herein can include one or more sensors such as an identification sensor (e.g., RFID, etc.), force sensors, motion sensors, position sensors. The data generated from such sensors can be connected to a developed signal conditioning unit interfaced through a software with machine learning algorithm (federated and global) deployed to the cloud (or in some cases executing at a local endpoint). The machine learning algorithms can interface with a unique federated learning architecture such that tool, sensor and surgeon specific data, are recognized, segmented and analyzed (signal, task, skill (through capturing position, orientation, force profile), pattern—all based on sensor signal), such that high fidelity feedback can be generated and provided in real-time (warning) or performance reporting (via secure application or online user profile).

With the wave of big data, sweeping across various industries, especially in the healthcare sector in which large volumes of data are preserved and owned by different centers and entities, computationally efficient and privacy-conserving solutions for universal and large-scale machine learning problems is pivotal. Centralized algorithms with the assumption of having principal repositories as a point of aggregation for all data contributors and centers, can be impractical in a scenario where non-centralized data locations, impede scalability to big data, and impose the risk of single point of failure leading to a situation where the integrity and privacy of the network data can be compromised. Due to access limitations, dealing with insufficient data, e.g., lack of full spectrum in possible anatomies and pathologies for an AI-based tumor identification model for instance, conventional machine learning models have shortfall in full capacity and will face blockage for transition from research to clinical application. In the medical applications, including operating room (OR)-based technologies where a network of data is widely spread across hospitals, a decentralized computationally scalable methodology is very much desired and necessary.

The efforts for establishing a connection between medical devices through Internet of Things (IoT) with the aim of accessing data in multiple nodes and processing for execution of specific tasks has shown a promise among the medical community. Data privacy and security had always been a hinderance for the evolvement of such an ecosystem as the data are stored in the isolated islands. The idea of Internet of Operating Theaters (IoT-OR), with the respective perks and complexities can fall into the same dilemma when it comes to data privacy. Medical data including electronic health record (EHR) and the information collected from a sensory-immersive operating room in individual institutions are segregated and stored in the local silos of data. Getting access to such data is difficult, deemed complex and slow due to security, privacy, regulatory, and operational issues.

Figure 1:
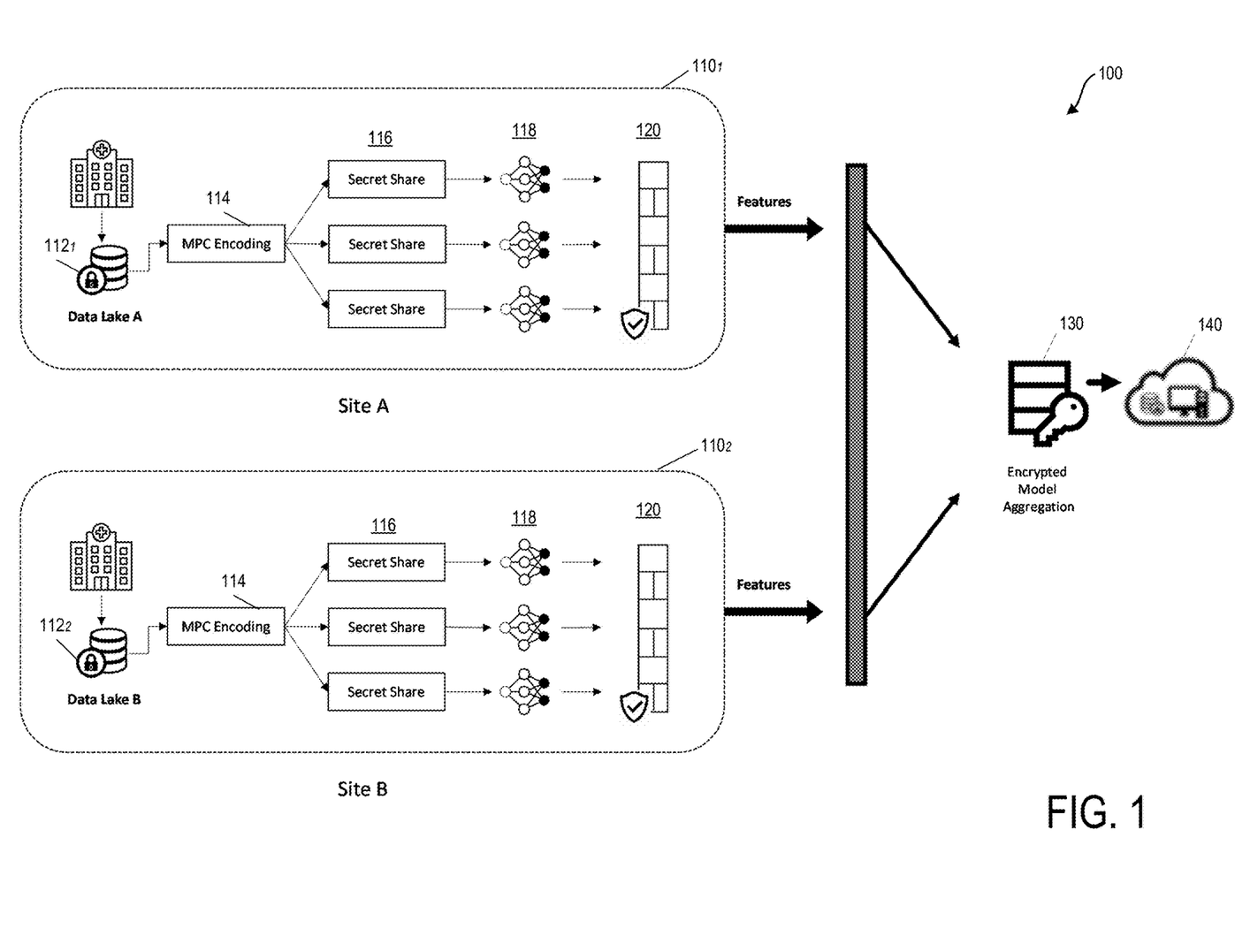
FIG. 1 is a diagram illustrating a model information aggregation framework across multiple sites through k-anonymity and homomorphic encryption.

With reference to diagram 100 of FIG. 1, federated learning, as provided herein, is a collaborative and lean machine learning model used in which multiple network connected medical devices at different surgical sites 110/ collaboratively learn machine learning models (two sites are illustrated for simplicity). Data characterizing aspects of such machine learning models (including extracted features, the local models themselves, model parameters and or other information, training status information, etc.) is used to inform a main model which can execute in the cloud or other central server (the term server as used herein can include a cluster of servers unless otherwise specified). The data from the machine learning models executing at the surgical sites $110_{1...n}$ can be encrypted 120 as part of the transport to the main model 140. Conversely, the main model 140 can send encrypted data (including extracted features, a central model, a global model, model parameters and information, training status information, etc.) to each of the surgical sites $110_{1...n}$ so that the local models can be accordingly updated. The encryption techniques can comprise k-anonymity and homomorphic encryption.

Each client site 110 can include a data lake 112 which can be a dedicated system or repository storing data derived from various network connected surgical instruments, medical devices, and other related equipment in connection with the care of patients. The data forming part of the data lakes 112 can be in various formats including structured and unstructured formats thereby avoiding data silos. The data in the data lakes 112 can be used for various purposes including machine learning and analytics for a wide variety of applications relating to patient care.

This technique supports decentralized collaborative machine learning over several devices or organizations (healthcare institutes/hospitals). The training data stays on each client device, e.g., a network-connected computing device within or in communication with a hospital operating theater including advanced medical devices (e.g., physiological sensors, sensor-equipped surgical instruments, etc.), and only the locally trained model parameters are transferred to a central coordinator which aggregates these models into a global federated model, e.g., through using the weighted average of the parameter values. The federated main model 140 can then sent back to the client devices at the respective surgical sites $110_{1...n}$ for training and improving their model iteratively. The privacy and sensitivity of data are protected as by keeping raw data on client devices at the respective surgical sites $110_{1...n}$.

In addition, federated learning as provided herein takes advantage of using computational resources of local client devices (i.e., the computing devices executed at the various surgical sites $110_{1...n}$) for time-consuming training of the model. In addition to ensure further confidentiality of all information and prevent indirect data leakage, the model parameters can be further secured through privacy preserving techniques like secure multi-party computation (MPC) encoding 114 in which a number of parties compute a joint function over the respective sensitive data sets and only the output of the joint function is disclosed without revealing the participants private data which can be stored locally or otherwise accessible in the data lakes $112_{1...n}$. by each client device (at each respective surgical site $110_{1...n}$). Through this technique, each sensitive data is split into secret shares 116 which in combination, yield the original data. The client devices as the surgical sites $110_{1...n}$ interact with each other to compute confidential function by exchanging secret shares 116 according to secure MPC encoding protocols. The split data through secret shares 116 can be trained locally using the segregated pieces of machine learning models 118 designed to learn the patterns in each secret share 116. The leaned features from the secret shares 116 can be transferred to the model aggregation server 130 and 140 after leaving the surgical site 110 through the security firewall 120.

A federated learning architecture as provided herein can help clinicians in diversifying patients information through data from other institutions and reduce diagnosis bias that occur toward certain demographic-based diseases, as they are often exposed to and managing a limited subgroup of patients from their local community. This will also benefit the patients in the way that high quality of clinical decisions are promised for all geographical locations and various levels in the economic scale.

In Internet-of-Things operating room (IoT-OR), also often termed digital operating room/theater paradigm, the composition of medical and surgical devices in the operating theater, including the surgical robotic devices, surgical microscope with video recording capability, surgical navigation system, and anesthesia monitoring system, and other similar vital signs monitoring devices including the intensive care unit (ICU) can be connected through an IoT-OR gateway (see FIG. 3) where the variables of interest (i.e., extracted features) are pre-analyzed before connecting to the cloud for data aggregation and inference through federated learning. In this framework, mini-AI models can be trained locally for each client device to allow for an individualized and system-based data models for separate applications, e.g., tumor identification through video data processing of microscope; surgical site sensor-based incoming information such as haptics (tool-tissue forces), optical, auditory, molecular etc., automated vital sign monitoring (anesthetic lines and probes providing for example blood gas information, cardio-respiratory, thermal, and other physiological information) and/or drug information and physiological response. Each user mini-AI model can be trained on a user's profile, e.g., a specific surgeon or anesthesiologist, and will be deployed on the cloud platform. This model specific arrangement can also be applied to recognition of patient information based on disease type, pre-operative diagnostic imaging or physiologic parameters for baseline characteristics, and that if consistent or altered during the procedure, input over time, to train the AI model. The main cloud model can learn and be re-trained from all individual models using federated learning to transfer feature sets to the cloud, recognize and segregate by patient or surgeon, without sharing data or cross-connecting, but high fidelity two way input-output based downstream deployment to prevent bias (FIG. 3).

Figure 2:
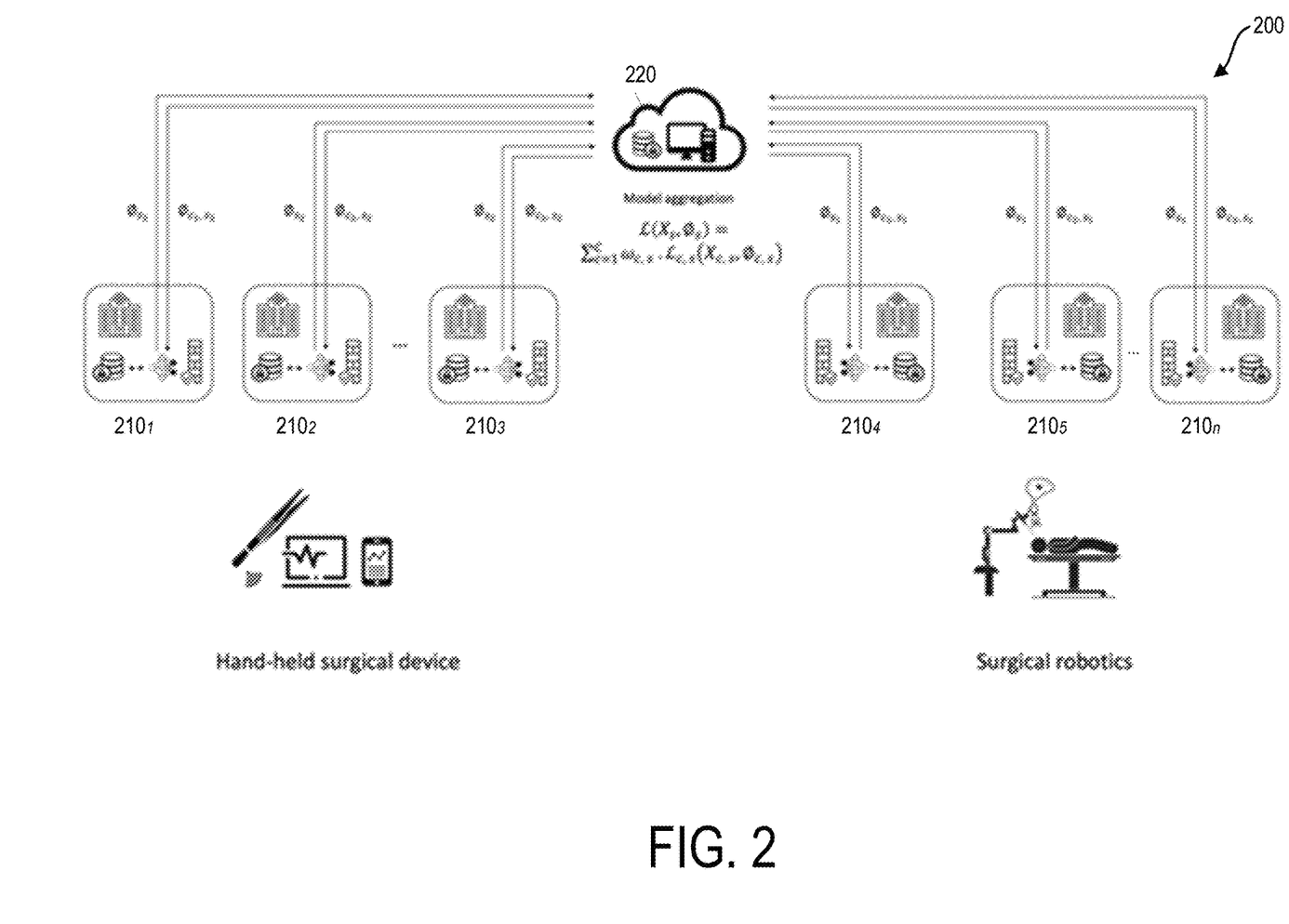
FIG. 2 is a first diagram illustrating a federated machine learning for interconnected surgical theater architecture.

FIG. 2 is a diagram 200 illustrated a federated learning workflow within the IoT-OR framework. The model for each client device $210_{1...n}$ (i.e., medical device, medical equipment, other sensors, etc.) can be trained periodically in each local institute and model parameters $\varnothing_{c,s}$ can be transmitted to a central model aggregation server 220 (e.g., a cloud computing environment, a dedicated server, etc.) for global learning. In this horizontal federated learning framework with decentralized data lakes and the central model aggregation server 220, the combined model parameters $\varnothing_s$ can be be transferred to each local client device $210_{1...n}$ for local inference.

As noted above, the client devices $210_{1...n}$ can take various forms and can range from handheld sensor-equipped surgical instruments, physiological sensors affixed to a patient, bedside patient monitors, robotic-assisted medical devices, fully automated robotic medical devices, and the like. For example, one of the client devices 210 can be a SmartForceps™ system which comprises sensorized surgical bipolar forceps that allows for real time record, display and monitor of forces of tool-tissue interaction during surgery), neuroArmPLUS™ telerobotic system and CelIARM™—a snakelike robotic endeffector that frees the problem of line of sight in surgery, enabling multiple data contributors and stakeholders to collaborate and converge to a common predictive model, without explicitly exchanging raw data. Each of the SmartForceps™ neuroArmPLUS™ telerobotic and CellArm™ system are products by and include trademarks of OrgSurgical, Ltd. of Calgary, Canada. Leveraging this technology with horizontal federated machine learning and secure MPC protocols, the sensitive training data can be kept locally on each medical device and only locally trained model parameters after k-anonymity and homomorphic encryption can be transferred to a central coordinator, for example, in a HIPAA (Health Insurance Portability and Accountability Act) compliant cloud which aggregates these models into a global federated model.

Figure 3:
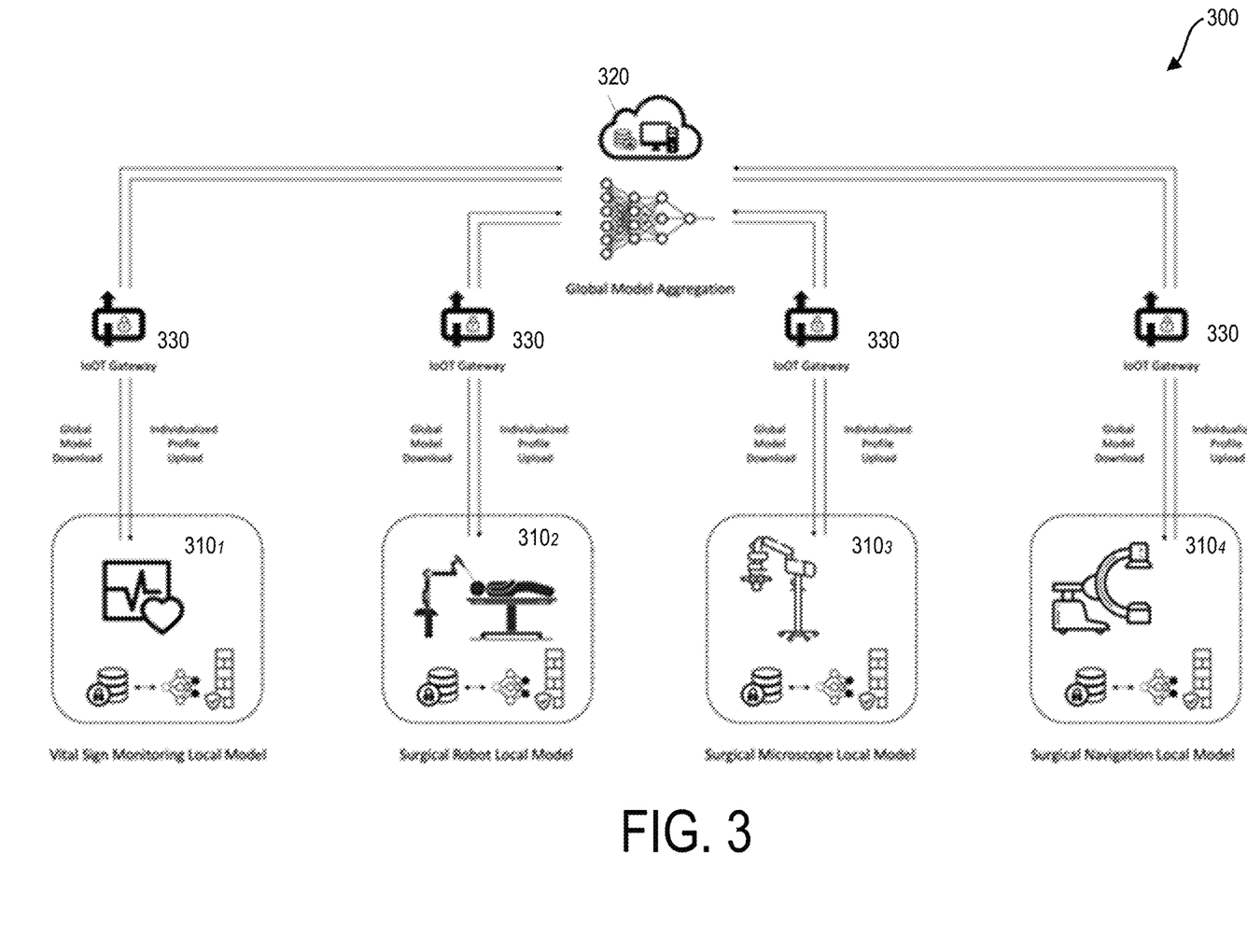
FIG. 3 is a second diagram illustrating a federated machine learning for interconnected surgical theater architecture.

Diagram 300 of FIG. 3 provides a schematic of the IoT-OR architecture which includes, as an example, four different client devices $310_{1...4}$ in which a first client device $310_1$ is configured to monitor vital signs of a patient (e.g., a physiological sensor, etc.) and executes a vital sign monitoring local model (i.e., a local model refers to a machine learning model), a second client device $320_2$ forms part of a surgical robot and executes a surgical robot local model, a third client device $320_3$ comprises a surgical microscope executing a surgical microscope local model, and a fourth client device $320_4$ comprises a surgical navigation system that executes a surgical navigation local model. Local model in this regard refers to one or more machine learning models (e.g., an ensemble of machine learning models, etc.) executing on the respective client device 310. The client devices 310 can interface with a remote cloud server 320 which aggregates, updates, and trains global models based on information, such as model parameters and profile information, passed from the client devices 310 over a respective IoT-OR gateway 320 to the cloud server 320. The cloud server 320 transmits the necessary data to the client devices 310 in order to update or otherwise deploy the respective local models. The IoT-OR gateway 320 can comprise various network interfaces to allow the various client devices 310 to exchange information wirelessly or via a wired connection with the cloud server 320. This element enables the local data storage and processing, and the ability to regularize the local feature transfer to/from the cloud server 320. The IoT-OR gateway 320 can comprise hardware or be a virtual device. The inclusion of an IoT-OR gateway 320 provides an extra level of security for data flow in and out of the medical systems through preventing data leaks and unauthorized control of the client devices 310 from outside parties. In some cases, the IoT-OR gateway 320 can analyze or otherwise process information received from the client devices 310 prior to transmission to the cloud server 320. Such an intelligent IoT-OR gateway 320, in addition to regulating data flow, can perform edge data analytics (extracting specific features and information) before sending the outputs to the cloud server 320.

With the architecture of FIGS. 1-3, a collaborative collection of sensory-immersive operating theaters transfers the specifics of training models to the cloud server 220, 320 (i.e., a central server in cases of an on-premise solution) without exchanging or centralizing data sets through federated learning paradigm. The formulation for such a paradigm in each technology may vary based on the model parameters, however, the general formulation is as follows:

$$\min_{\emptyset} \mathcal{L}(X, \emptyset), \mathcal{L}(X, \emptyset) = \sum_{c=1}^{C} \omega_c \cdot \mathcal{L}_c(X_c, \emptyset_c),$$

where $\mathcal{L}$ is the loss function combining C various centers (e.g., surgical site, hospital area, etc.). Each client device 320 contributes to the federated model and calculated for each individual center c based on the local private data $X_c$ through a set of weights coefficients $\omega_c$.

The following provides an example with regard to a particular type of client device 320, namely a SmartForceps™, hand-held sensor equipped medical device (and further exemplary details are in U.S. patent application Ser. No. 17/318,975 filed on May 14, 2021, which as noted above, is fully incorporated by reference).

Figure 4:
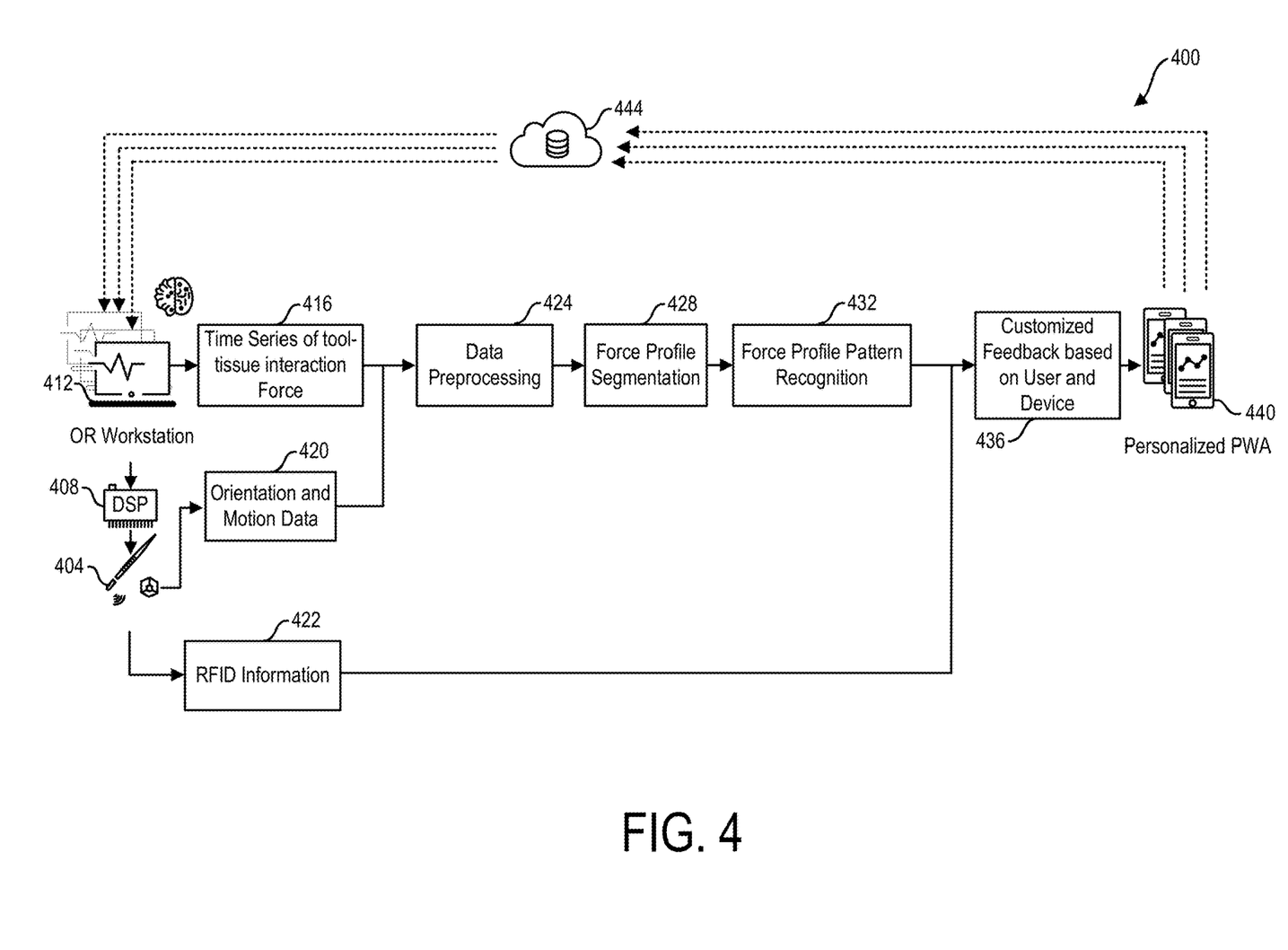
FIG. 4 is a diagram illustrating a federated machine learning technique as applied to surgical theaters utilizing sensor-equipped surgical tools.

FIG. 4 is an example architecture diagram 400 which comprises a sequence two or more machine learning models that can interact with a surgical instrument. In this example, the surgical instrument is a sensor-equipped forceps 404; however, it will be appreciated that other types of surgical instruments can be used. In addition, while the example of FIG. 4 includes two machine learning models executing in sequence, it will be appreciated that a different ensemble and/or architecture of two or more machine learning models can be used depending on the desired configuration including, for example, the type of data being generated by the surgical instrument and/or other types of complementary data being generated by other medical devices or instruments within a surgical setting (e.g., an operating room).

Referring again to FIG. 4, a surgical instrument 404 (i.e., a sensor-equipped surgical can communicate with one or more computing devices including an operating room workstation 412 by way of a communications interface 408 such as a digital signal processor (e.g., a DSP for conditioning data generated by strain gauge sensor). The surgical instrument 404 through its sensors, generates one or more data streams that characterize the use of the surgical instrument (in general and in relation to a patient). These data streams can take various forms and can be provided directly, or indirectly (e.g., via the operating room workstation 412) to a consuming application or process. A first data stream 416 can provide time-series data characterizing tool-tissue interaction force (e.g., derived from a strain gauge sensor on the surgical instrument 404, etc.). A second data stream 420 can provide data characterizing the orientation and motion of the surgical instrument 404 (e.g., derived from a inertial measurement unit sensor on the surgical instrument, etc.). In addition, identification information 422 can also be provided. This identification information can, for example, be derived from an RFID or similar sensor on the surgical instrument.

Data from the first and second data streams 416, 420 can be pre-processed 424 in a variety of manners. Pre-processing can include labeling the data, filtering out noise, removing outliers, and/or extracting features from the data streams. The noise reduction can, for example, be performed using a Butterworth low-pass filter and outliers can be removed based on the 1st and 99th percentile thresholds of expert force profiles as <1% error was assumed to occur by experienced surgeons. Features that can be extracted include those referred to above as well as one or more of e.g., force maximum, range, coefficient of variance, peak counts and values, cycle length, signal fluctuations and entropy, and flat spots, and the like.

A first machine learning model 428 (e.g., a force profile segmentation model, etc.) can take the pre-processed data (i.e., the cleaned force time-series data, extracted features, etc.) to construct force profile comprising a plurality of force patterns. The first machine learning model 428 can take various forms and, in one example, can be a U-Net model comprising a convolutional encoder and decoder structure to capture the properties and reconstruct the force profile (X_in∈ R^(S_0×i×C):S_0 fixed-length segment interval each containing i data points through C=2 channels for left and right prong) through a deep stack of feature maps followed by a mean-pooling-based classifier on point-wise confidence scores for interval-wise time series segmentation (X_(seg.)∈R^(S×K): S final segment intervals containing K=2 segment classes, i.e. device on/off).

A second machine learning model 432 can characterize force profile pattern recognition. The output of this second machine learning model 432 can be used to directly or indirectly characterize surgical experience level. In other words, the output of the second machine learning model 432 can be used as part of an algorithm to classify surgeon experience level (i.e., novice, intermediate, and expert) and allocate surgical competency scores based on descriptive force patterns, high force error, low force error, variable force, and other unsafe force instances.

The second machine learning model 432 can, for example, be a neural network or ensemble of neural networks. In one variation, the second machine learning model 432 comprises a deep neural network model for time series classification based on 33 InceptionTime to obtain learned features that together with engineered features such as described above can be used in a logistic regression-based surgeon experience classification. The input to the network can be a segmented force time-series (X_(seg.)∈R^(S×C): S segment intervals over C=2 channels of left and right prong data in sensor-equipped forceps). The network can comprise multiple layers including a bottleneck layer to reduce the dimensionality, a series of convolutional layers to learn the features followed by connection layers, and a max pooling layer. The output of the network can be probabilities of different classes, i.e., surgical proficiency scores.

In addition or in some variations, the output of the second machine learning model 432 can be used to identify or otherwise characterize surgical task type (for example, by a third machine learning model). This can be based on a time-series based surgeon activity recognition while performing a specific task (i.e., coagulation, dissection, pulling, retracting, and manipulating). A recurrent neural network based on LSTM can be used in this regard that includes an input layer for the segmented force data (X_(seg.)∈R^(S× C)), hidden layers with ReLU activation to interpret the extracted features, and a dropout regularization layer, a ReLU activation layer, and an output layer with Softmax activation providing the probability distribution of each surgical task class. The network weights Θ which characterizes the behavior of transformations can be identified through nonlinear optimization methods e.g., gradient descent and adam, to minimize the loss function, e.g., categorical cross entropy, in the training data and backpropagation of error throughout the network for updating the weights.

The output of the first and second machine learning models 428, 432 can be used to provide feedback 436 to the user of the surgical instrument 404 (e.g., a surgeon, etc.). The feedback can be provided in various manners including haptic, audio, visual (e.g., a heads up display, etc.) and/or on an endpoint computing device 440 (e.g., a mobile phone, a tablet, a computer, etc.). The real-time feedback can be generated after incorporating the sensory input data (IMU: orientation and motion details—Strain Gauge: tool-tissue interaction force—RFID: radio-frequency identification for the unique tool specs (tool type (forceps, dissector, suction device, etc.), tool length, tip size, calibration factor, manufacturing date, etc.)) into the first and second machine learning models 428, 432 and the output can be customized based on the user skill and tool type. The feedback can be provided, for example, when there is an unsafe event so that the surgeon can take appropriate remedial action.

The feedback provided by the current subject matter can take various forms and have different granularity. The output of one or more of the first and second machine learning models 428, 432 can be used to specify how a particular user is performing relative to their own past performance, how that particular user is performing relative to his or her peers within a particular group (e.g., hospital), how that particular user is performing across all surgeons, and the like. In some cases, there can be different levels/groupings such as trainee—master—peers and that these groups may have their own associated first and second machine learning models 428, 432 which are used to provide feedback (whether in real-time or post-surgery procedure).

One or more of the first and second machine learning models 428, 432 can be updated or otherwise trained using a federated learning procedure (such as that described above) which utilizes data generated by multiple surgical instruments 404 across different users and/or across different locations. The machine learning model parameters transported to the cloud 444 as part of the federated learning procedure can be de-identified, encrypted (e.g., homomorphically encrypted, etc.) prior it to be being transported over the network.

The outputs of these models can include the model parameters $\emptyset_{s,c}$ with the input data of $X_{model}$. The model for SmartForceps™ device in center c ($\emptyset_{s,c}$) will be $\mathcal{L}_{s,c}$ ($X_{model,c}$, $\emptyset_{s,c}$) and the aggregation across different centers can be:

$$\mathcal{L}(X_{model}, \emptyset_s) = \sum_{c=1}^{C} \omega_c \cdot \mathcal{L}_{s,c}(X_{model,c}, \emptyset_{s,c}).$$

As noted above, data or model parameters can be encrypted using homomorphic encryption in which the subsequent computations, e.g., SmartForceps data transformations along with feature extraction for machine learning models, can be performed directly on encrypted data, having identical results after decryption with a situation where no encryption was in place. This approach adds an extra level of security compared to traditional encryption methods, e.g., advanced encryption standard (AES) which is fast, however, require decryption before any operations on data, thus rising security concerns specially for healthcare-related data.

Implementing this technique for IoT-OR-generated data will encompass unique specifications. Prior to homomorphic encryption, the patient personal data, e.g., name, demographics, disease information, etc., and surgeon personal data, e.g., name, skill, etc., will be obfuscated to unidentifiable codes and the translation keys will be kept within the medical center database and firewall. In the next step, where no human private data is available and in cases where selective data should be transferred to the cloud, the device generated data, e.g., force data from SmartForceps, will be encrypted by homomorphic method using Microsoft SEAL libraries and further computations and model improvements can take place in the model aggregation server within the HIPAA-compliant Microsoft Azure platform. Following machine learning model developments on encrypted data, the encrypted results or updated model parameters will be transferred back to multiple-party data owners or the edge computing devices for future implementations and model inferences.

Ring-Learning with Errors (RLWE), which is based on the mathematics of high-dimensional lattices, will be used for ensuring the security of homomorphic encryption scheme, making the algorithm robust against quantum computers.

In addition to homomorphic encryption, k-anonymity encryption can be utilized. This encryption model will further ensure the privacy of shareable model parameters or selective information between multiple medical centers by only releasing a version of data that cannot be re-identified by the entities sharing the aggregated model or information. k-anonymity encryption protects information of each entity or data holder contained in the aggregated model release from being distinguished by at least k−1 medical centers whose information also appears in the release.

k-anonymity encryption uses the following methods to protect the privacy of the data holder:

Suppression: Using this, certain values of the attributes and columns in the anonymized table are replaced by an asterisk '*' while all or some values of a columns may be replaced by '*'.

Generalization: Using these individual values of attributes are replaced with a broader category. For example, the value 'X=6' of the attribute 'Experience' may be replaced by '>5', the value 'Y=20' by '10<Experience≤30', etc.

Figure 5:
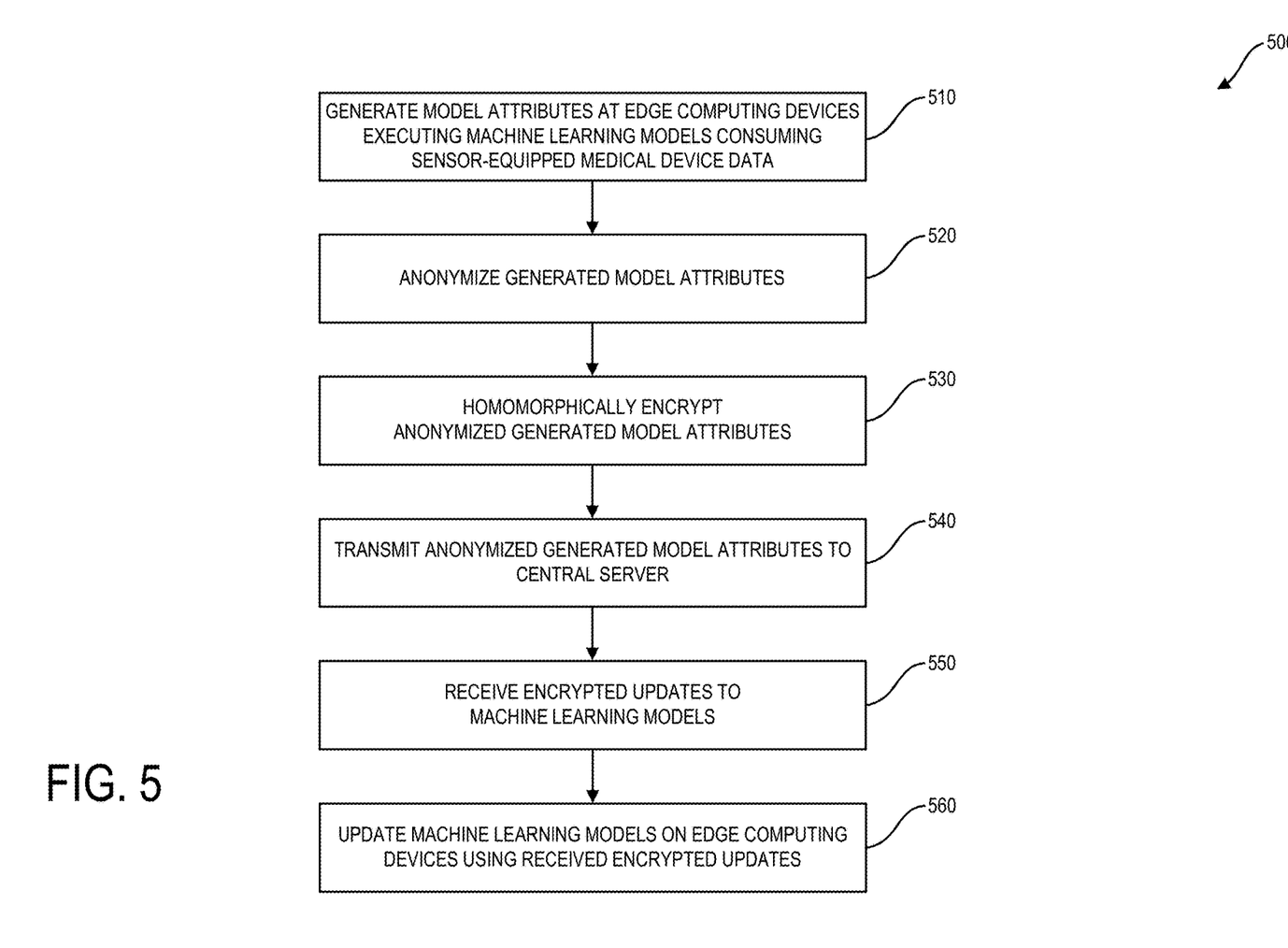
FIG. 5 is a first process flow diagram illustrating a federated machine learning technique as applied to surgical theaters.

FIG. 5 is a diagram 500 in which, at 510, each of a plurality of edge computing devices generate model attributes. Each of the edge computing devices are configured to receive one or more data streams generated by at least one sensor forming part of a respective medical device. The at least one sensor characterizes use of the respective medical device in relation to a particular patient. In addition, each of the edge computing devices executes at least one machine learning model. Thereafter, at 520, the generated model attributes are anonymized using, for example, k-anonymity. The anonymized generated model attributes are then, at 530, homomorphically encrypted. The anonymized generated model attributes are then transmitted, at 540, to a central server. Later, at 550, encrypted model attribute updates to at least one of the machine learning models which are based on the transmitting are received from the central server. Based on these updates, at 560, one or more of the machine learning models executing on one or more of the edge computing devices are updated.

Figure 6:
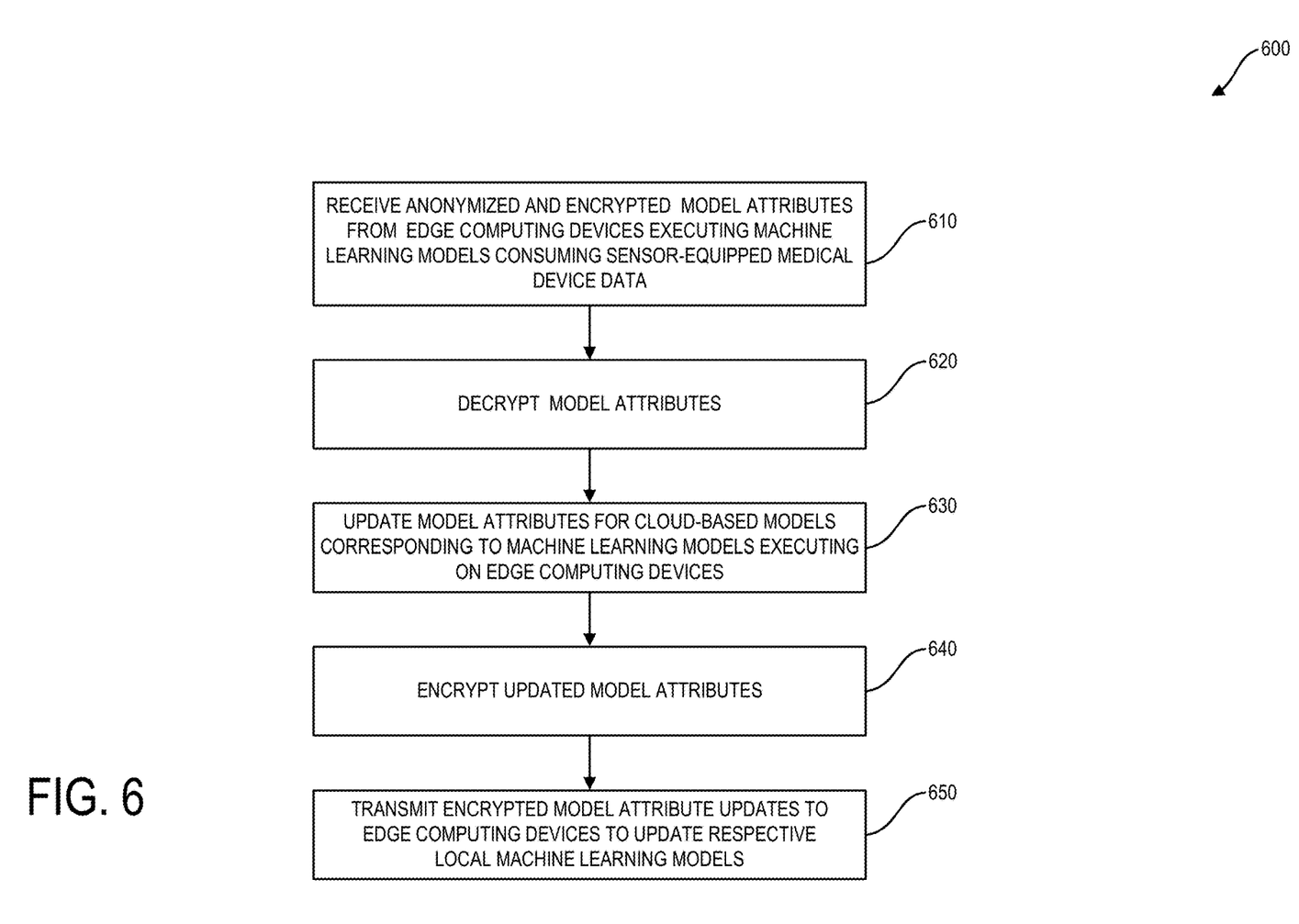
FIG. 6 is a second process flow diagram illustrating a federated machine learning technique as applied to surgical theaters.

FIG. 6 is a diagram 600 in which, at 610, anonymized and encrypted model attributes are received by a cloud server from each of a plurality of edge computing devices. Each of the edge computing devices are configured to receive one or more data streams generated by at least one sensor forming part of a respective medical device. The at least one sensor characterizes use of the respective medical device in relation to a particular patient. In addition, each of the edge computing devices executes at least one machine learning model. Subsequently, at 620, the received model attributes are decrypted. The cloud server, at 630, updates model attributes for one or more cloud-based machine learning models corresponding to one or more machine learning models being executed by the edge computing devices. These updated model attributes are, at 640, encrypted by the cloud server. The cloud server, at 650, transmits the encrypted updated model attributes to the edge computing devices executing at least one machine learning model having updated model parameters so that the corresponding edge computing device can decrypt the updated model attributes and update the corresponding machine learning models based on the transmitted updated model parameters.

The model attributes can take various forms including hyperparameters. Model hyperparameters in this regard can include, for example, one or more of: neural network hidden layer size, number of convolution layers, batch normalization specifications, activation layer type, and the like. The model attributes can alternatively or additionally include model information such as one or more of: model name, data input and output characteristics, data dimensionality, training data size, testing data size, number of training iterations, learning rate, or optimization method.

The updating of the machine learning models can take various forms. In some cases, the local models can be retrained using the received encrypted updates (e.g., encrypted model hyperparameters, etc.) or data derived from therein.

Various implementations of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and may be implemented in a high-level procedural and/or object-oriented programming language, and/or in assembly/machine language. As used herein, the term "machine-readable medium" refers to any computer program product, apparatus and/or device (e.g., magnetic discs, solid state drives, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the subject matter described herein may be implemented on a computer having a display device (e.g., a CRT (cathode ray tube) or LCD (liquid crystal display) monitor) for displaying information to the user and a keyboard and a pointing device (e.g., a mouse or a trackball) by which the user may provide input to the computer. Other kinds of devices may be used to provide for interaction with a user as well; for example, feedback provided to the user may be any form of sensory feedback (e.g., visual feedback, auditory feedback, or tactile feedback); and input from the user may be received in any form, including acoustic, speech, or tactile input.

The subject matter described herein may be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), and the Internet.

The computing system may include clients and servers. A client and server are generally remote from each other and typically interact through a communication network. The relationship of client and server arises by virtue of computer programs running on the respective computers and having a client-server relationship to each other.

Although a few variations have been described in detail above, other modifications are possible. For example, the logic flow depicted in the accompanying figures and described herein do not require the particular order shown, or sequential order, to achieve desirable results. Other embodiments may be within the scope of the following claims.

What is claimed is:

1. A method comprising:
  generating, by each of a plurality of edge computing devices, model attributes, each of the edge computing devices configured to receive one or more data streams generated by at least one sensor forming part of a respective medical device, the at least one sensor characterizing use of the respective medical device in relation to a particular patient, each of the edge computing devices executing at least one machine learning model;

anonymizing the generated model attributes using k-anonymity;

homomorphically encrypting the anonymized generated model attributes;

transmitting the anonymizing generated model attributes to a central server;

receiving encrypted model attribute updates to at least one of the machine learning models from the central server based on the transmitting; and updating one or more of the machine learning models executing on one or more of the edge computing devices based on the received encrypted model attribute updates.

2. The method of claim 1, wherein the model attributes comprise model hyperparameters.

3. The method of claim 2, wherein the model hyperparameters comprise one or more of: neural network hidden layer size, number of convolution layers, batch normalization specifications, or activation layer type.

4. The method of claim 1, wherein the model attributes comprise model information.

5. The method of claim 4, wherein the machine learning model information can comprise one or more of: model name, data input and output characteristics, data dimensionality, training data size, testing data size, number of training iterations, learning rate, or optimization method.

6. The method of claim 1, wherein the updating comprises: retraining the one or more of the machine learning models executing on one or more of the edge computing devices using the received encrypted updates.

7. The method of claim 6, wherein the received updates comprise: encrypted model hyperparameters.

8. A method comprising:

receiving, by a cloud server from each of a plurality of edge computing devices, anonymized and encrypted model attributes, each of the edge computing devices configured to receive one or more data streams generated by at least one sensor forming part of a respective medical device, the at least one sensor characterizing use of the respective medical device in relation to a particular patient, each of the edge computing devices executing at least one machine learning model;

decrypting the received model attributes;

updating, by the cloud server, model attributes for one or more cloud-based machine learning models corresponding to one or more machine learning models being executed by the edge computing devices;

encrypting the updated model attributes; and transmitting the encrypted updated model attributes to the edge computing devices executing at least one machine learning model having updated model attributes, the corresponding edge computing device decrypting the updated model attributes and updating the corresponding machine learning models based on the transmitted updated model attributes.

9. The method of claim 8, wherein the model attributes comprise model hyperparameters.

10. The method of claim 9, wherein the model hyperparameters comprise one or more of: neural network hidden layer size, number of convolution layers, batch normalization specifications, or activation layer type.

11. The method of claim 8, wherein the model attributes comprise model information.

12. The method of claim 11, wherein the machine learning model information can comprise one or more of: model name, data input and output characteristics, data dimensionality, training data size, testing data size, number of training iterations, learning rate, or optimization method.

13. The method of claim 8, wherein the updating comprises: retraining the one or more of the machine learning models executing on one or more of the edge computing devices using the received encrypted updates.

14. The method of claim 13, wherein the received updates comprise: encrypted model hyperparameters.

15. A system comprising:

a plurality of edge computing devices each configured to receive one or more data streams generated by at least one sensor forming part of a respective medical device, the at least one sensor characterizing use of the respective medical device in relation to a particular patient, each of the edge computing devices executing at least one machine learning model; and a cloud-based computing system for training and updating the respective at least one machine model based on data received from the plurality of edge computing devices which has been anonymized and encrypted using homomorphic encryption prior to it being transmitted over a network by the edge computing devices, the cloud-based system sending updates over the network to the machine learning models.

16. The system of claim 15 further comprising:

a plurality of Internet of the Operating Theaters (IoT-OR) gateways providing communication interfaces between the edge computing devices and the cloud-based computing system to allow for the exchange of model attributes used for updating the respective machine learning models.

17. The system of claim 16, wherein the model attributes comprise model hyperparameters.

18. The system of claim 17, wherein the model hyperparameters comprise one or more of: neural network hidden layer size, number of convolution layers, batch normalization specifications, or activation layer type.

19. The system of claim 16, wherein the IoT-OR gateways relay data from the edge computing devices to the cloud-based computing system.

20. The system of claim 16, wherein the IoT-OR gateways process data from the edge computing devices prior to transmission to the cloud-based computing system.

* * * * *